United States Patent [19]
Mason

[11] Patent Number: 5,354,924
[45] Date of Patent: Oct. 11, 1994

[54] PROCESS FOR THE PRODUCTION OF DINITROTOLUENE

[75] Inventor: Robert W. Mason, Lake Charles, La.

[73] Assignee: Olin Corporation, Cheshire, Conn.

[21] Appl. No.: 108,035

[22] Filed: Aug. 17, 1993

Related U.S. Application Data

[63] Continuation of Ser. No. 900,213, Jun. 17, 1992, abandoned, which is a continuation-in-part of Ser. No. 210,549, Jun. 22, 1988, abandoned.

[51] Int. Cl.$^5$ .......................................... C07C 205/11
[52] U.S. Cl. .................................................. 568/934
[58] Field of Search ............... 568/934, 937, 932, 939, 568/940

[56] References Cited

U.S. PATENT DOCUMENTS

| | | | |
|---|---|---|---|
| 2,362,743 | 11/1944 | Crater | 568/934 |
| 2,739,174 | 3/1956 | Ross | 260/645 |
| 2,864,871 | 12/1958 | Morningstar | 568/932 |
| 3,293,310 | 12/1966 | Picard et al. | 260/645 |
| 3,434,802 | 3/1969 | Toischer et al. | 23/260 |
| 3,780,116 | 12/1973 | Sahgal | 260/645 |
| 3,928,395 | 12/1975 | Seha et al. | 522/253 |
| 3,976,704 | 8/1976 | Vaughan | 260/645 |
| 4,028,425 | 6/1977 | Gilbert | 568/934 |
| 4,064,147 | 12/1977 | Thelen et al. | 260/369 |
| 4,112,005 | 9/1978 | Thiem et al. | 260/645 |
| 4,123,466 | 10/1978 | Lin et al. | 260/645 |
| 4,261,908 | 4/1981 | Schroeder et al. | 260/369 |
| 4,347,389 | 8/1982 | Schumacher et al. | 568/937 |
| 4,415,744 | 11/1983 | Schumacher et al. | 560/20 |
| 4,418,230 | 11/1983 | Bakke et al. | 568/940 |
| 4,426,543 | 1/1984 | Schumacher et al. | 568/940 |
| 4,465,876 | 8/1984 | Milligan | 568/940 |
| 4,469,904 | 9/1984 | Wang et al. | 569/948 |
| 4,551,568 | 11/1985 | Sato et al. | 568/939 |
| 4,600,702 | 7/1986 | Schumacher | 502/200 |
| 4,618,733 | 10/1986 | Schumacher | 568/927 |
| 4,621,157 | 11/1986 | McDaniel | 568/932 |
| 4,628,131 | 12/1986 | Schumacher | 568/937 |
| 4,935,557 | 6/1990 | Carr et al. | 568/934 |
| 5,057,632 | 10/1991 | Imm et al. | 568/934 |

*Primary Examiner*—Robert L. Stoll
*Assistant Examiner*—Valerie D. Fee
*Attorney, Agent, or Firm*—Dale L. Carlson

[57] ABSTRACT

Aromatic nitration reactions and, more specifically, a process for nitrating toluene to produce dinitrotoluene in the absence of any dipolar aprotic solvent.

14 Claims, No Drawings

PROCESS FOR THE PRODUCTION OF DINITROTOLUENE

This application is a continuation of application Ser. No. 07/900,213, filed Jun. 17, 1992, now abandoned, which is a continuation-in-part of U.S. Ser. No. 07/210,549, filed, Jun. 22, 1988, now abandoned.

FIELD OF THE INVENTION

This invention relates generally to aromatic nitration reactions and, more specifically, to a process for nitrating toluene to dinitrotoluene.

BACKGROUND OF THE INVENTION

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition, the use of sulfuric acid tends to result in significant nitrocreosol and cyanide by-product formation which requires expensive waste-water treatment to remove.

In view of these disadvantages associated with mixed nitric/sulfuric acid systems, there have been recent attempts to perform gas phase or liquid phase nitrations in concentrated nitric acid in the absence of sulfuric acid. By way of illustration, U.S. Pat. No. 4,064,147 discloses the preparation of aromatic mononitro compounds (such as mononitrobenzene) by a liquid phase reaction with nitric acid having an acid concentration of between 70 percent and 100 percent by weight using a reaction temperature of between 0° C. and 80° C. When employing a relatively reactive compound such as benzene or toluene as a starting material, this patent teaches that a nitric acid concentration of between 70 and 90 percent by weight is preferred. The disclosure of this patent requires a ratio of nitric acid plus water to organic components of not below 3 when using 70 percent nitric acid, and not below 8 when using 100 percent nitric acid.

As another illustration, U.S. Pat. No. 3,928,395 discloses the use of concentrated nitric acid to nitrate aromatic compounds optionally in the presence of a dipolar aprotic solvent that is inert towards the nitrating agent. The patent requires that reaction be halted by diluting the resulting mixture with a dipolar aprotic solvent after the desired degree of nitration has been reached. Unfortunately, the use of such solvents either throughout the reaction or to halt the reaction tends to cause environmental waste disposal problems and waste stream handling problems.

Since dinitrotoluene is useful as an intermediate in producing TDI, new processes for the selective manufacture of this intermediate while avoiding the above mentioned problems would be highly desirable to the polyisocyanate manufacturing community.

SUMMARY OF THE INVENTION

The present invention relates to a process for nitrating toluene to produce dinitrotoluene by a liquid phase nitration reaction of anhydrous nitric acid with toluene in a reactor at a reaction temperature of between 0° C. and 60° C. for a reaction time of less than 15 minutes, said reaction employing a molar ratio of nitric acid plus any water to toluene of between 10:1 and 15:1, said reacion being conducted in the absence of sulfuric acid, and in the absence of any aprotic dipolar solvent during the reaction and in the absence of any aprotic dipolar solvent to halt the reaction, to produce mononitrobenzene or dinitrotoluene in a product mixture to produce said dinitrotoluene in a product mixture, followed by vacuum distillation of the product mixture, in the absence of any aprotic dipolar solvent, to remove unreacted nitric acid from said product mixture thereby providing said dinitrotoluene.

This and other aspects of the present invention will become apparent upon reading the following detailed description of the invention.

DETAILED DESCRIPTION OF THE INVENTION

In accordance with the process of the present invention, the nitration reaction is conducted using anhydrous nitric acid in the absence of sulfuric acid. As used herein, the term "anhydrous nitric acid" is intended to designate nitric acid having an acid concentration of between 95 and 100 weight percent, preferably at least 98 weight percent, the remainder being water. It is desirable to minimize the amount of water in the reaction mixture since water (a) causes the nitration reaction to stop at the mononitration stage in toluene reaction and (b) prevents the nitration of benzene to mononitrobenzene.

The process of the present invention utilizes a one-step reaction in a single phase liquid medium and does not involve the formation of the two phase emulsions observed in conventional, mixed sulfuric/nitric acid nitration processes. Another surprising aspect of this invention is that the reaction can be conducted under moderate reaction conditions to provide an excellent yield of the desired mononitrobenzene or dinitrotoluene product. Thus, the reaction is suitably conducted at a reaction temperature not exceeding 80° C., preferably between 0° C. and 60° C., more preferably between 10° C. and 60° C., most preferably between 20° C. and 30° C. The reaction is suitably conducted at atmospheric pressure, although superatmospheric pressure can be employed if desired. The reaction time is typically less than one-half hour, preferably less than 15 minutes, and more preferably less than 5 minutes.

For the reaction of toluene to dinitrotoluene, the molar ratio of nitric acid plus water to toluene employed is generally between 10:1 and 15:1, preferably between 11:1 and 12:1.

Operating within the above-recited broad ranges of molar ratios (and particularly within the preferred ranges) maximizes the production of the desired product and minimizes by-product formation.

After reaction and product formation, it is desired that excess (unreacted) nitric acid be removed from the reactor, preferably by vacuum distillation, thus providing a low temperature, low pressure distillation. Suitable distillation temperatures range from 30° C. to 60° C. Suitable distillation pressures range from 50 mm of Hg to 300 mm of Hg.

Following removal of the excess anhydrous nitric acid, DNT separation from the distillation still bottoms can be effected by phase separation, brought about by the addition of a small quantity of water or dilute nitric acid. Washing with water and a basic solution produces a purified DNT product. These wash waters are free of the nitrocresol impurities observed in the wastewater produced in a conventional, mixed sulfuric/nitric acid DNT process. The aqueous nitric acid from the phase separation step can be purified by toluene extraction, the toluene phase being recycled to the reaction step and the 60-70% aqueous nitric acid phase reconcentrated, sold or used in other product manufacture.

The following examples are intended to illustrate, but in no way limit the scope of, the present invention.

EXAMPLE 1

Synthesis of Dinitrotoluene

A four milliliter glass vial, equipped with a magnetic stir bar and a silicone septum, was immersed in a water bath. The reaction vial was flushed with nitrogen at a rate of 20 cc/min, purging to a 100 ml glass receiving flask immersed in an ice water bath. To the reaction vial was fed 50 ml of 98 percent $HNO_3$, 75.0 g, 1.13 mole of $HNO_3$ and 10 ml, 8.67 g, 0.094 mole of toluene. Feed rates were 0.60 ml $HNO_3$/min and 0.12 ml toluene/min, controlled by Sage Instrument Syringe pumps, Models 351 and 355. Reactor content was adjusted to 2 ml, by height adjustment of the reactor exit line in the reaction vial, for a mean reaction residence time of 2.8 minutes. The reactor water bath was maintained at 15°±5° C. by the periodic addition of ice during reactant addition. Upon completion of the reactant addition, the reactor contents were stirred for 3 minutes, then purged to the receiver. A total of 83.31 g of pale yellow product solution was obtained. Distillation of this solution (53° C., 75-160 mmHg) gave 38.75 g of pale yellow acid which analyzed, by titration with standardized NaOH, as 100 percent $HNO_3$. The pot contained 44.21 g of pale yellow solution; 0.42 g of $HNO_3$ was lost to the walls of the glassware, leaving an estimated 0.43 g of product lost to $NO_2$ vapors during the distillation. The pot solution was diluted with 21.72 g of water and extracted with 33.30 g of toluene. Separation of the layers furnished 48.74 g of weak, aqueous acid and 48.11 g of toluene/DNT solution. The organic layer was washed once with 20 ml of water, then dried over $MgSO_4$ and filtered. DNT recovery was calculated at 86 percent, with a normalized GC analysis of 0.02 weight percent 4-nitrotoluene, 17.36 percent 2,6-DNT, 0.48 percent 2,5-DNT, 78.47 percent 2,4-DNT, 1.65 percent 2,3-DNT, 1.92 percent 3,4-DNT and 0.09 percent TNT. $HNO_3$ accountability, as recovered weak acid and DNT equivalent, was 99 percent.

EXAMPLE 2

Additional Syntheses of Dinitrotoluene

In the manner described in EXAMPLE 1, 100 ml of 98 percent $HNO_3$, 150.0 g, 2.38 mole $HNO_3$ and 21 ml, 18.2 g, 0.20 mole of toluene were fed at 0.80 ml/min and 0 0.17 ml/min, respectively, to the reaction vial. A total of 166.26 g of pale yellow product solution was obtained. The product was heated for two hours at 55° to 60° C., then cooled and diluted with 46.5 g of ice water. The resulting suspension was extracted once with 41.5 g of toluene and then a second time with 46.3 g of toluene. The combined toluene extract was extracted with 3×15 ml of 5 percent sodium hydroxide solution. The combined, yellow caustic extract was cooled, acidified with dilute sulfuric acid, and extracted with 3×10 ml of methylene chloride. After evaporation of the bulk of the methylene chloride, the methylene chloride extract, containing the acidic organic species from the original DNT product, was characterized by gas chromatography/mass spectrometry analysis. No mononitro- or dinitro-cresol species were detected (minimum detectability calculated at 2 ppm, based on original weight of DNT produced).

Additional experiments were performed to define the reactant ratio suitable for selective DNT synthesis. These products are characterized in TABLE I below for various molar ratios of $HNO_3$ to toluene.

TABLE I

| | Toluene Nitration | | | | | |
|---|---|---|---|---|---|---|
| | $HNO_3$/Toluene | | | | | |
| | Mole | Wt. | Product in Wt. % | | | |
| Sample | Ratio | Ratio | o-NT | m-NT | p-NT | DNT |
| 1 | 3.4 | 2.3 | 53.17 | 4.04 | 39.29 | 3.49 |
| 2 | 5.6 | 3.8 | 28.80 | 2.70 | 29.57 | 38.93 |
| 3 | 7.8 | 5.3 | 8.21 | 1.72 | 14.66 | 75.40 |
| 4 | 11.6 | 7.9 | 0.94 | — | 0.22 | 98.84 |

Reaction at 54° to 57° C.
NT - mononitrotoluene, ortho, meta and para isomers

What is claimed is:

1. A process for nitrating toluene to produce dinitrotoluene by a liquid phase nitration reaction of nitric acid with toluene in a reactor at a reaction temperature of between 0° C. and 60° C. for a reaction time of less than one-half hour and at reaction pressure not exceeding atmospheric pressure, said reaction employing a molar ratio of nitric acid plus any water to toluene of between 10:1, and 15:1, said reacion being conducted in the absence of sulfuric acid, and in the absence of any aprotic dipolar solvent during the reaction and in the absence of any aprotic dipolar solvent to halt the reaction, to produce said dinitrotoluene in a product mixture that is free of mononitro- and dinitro- cresol species, followed by vacuum distillation of the product mixture, in the absence of any aprotic dipolar solvent, to remove unreacted nitric acid from said product mixture thereby providing said dinitrotoluene.

2. The process of claim 1 wherein said molar ratio is between 11:1 and 12:1.

3. The process of claim 1 wherein said anhydrous nitric acid has an acid content of between 95 percent and 100 percent by weight based upon the acid plus water therein.

4. The process of claim 1 wherein said vacuum distillation is effected at a temperature of between about 30° C. and about 60° C.

5. The process of claim 1 wherein said vacuum distillation is effected at a pressure of between about 50 mm of Hg and about 300 mm of Hg.

6. The process of claim 1 which additionally comprises, after said vacuum distillation, phase separation of dinitrotoluene from said product mixture.

7. The process of claim 6 wherein said phase separation is caused by the addition of water or dilute nitric acid to said product mixture.

8. The process of claim 1 wherein said reaction temperature is between 10° C. and 60° C.

9. The process of claim 1 wherein said reaction temperature is between 20° C. and 30° C.

10. The process of claim 1 wherein said nitration reaction is effected in less than 5 minutes.

11. The process of claim 1 wherein said anhydrous nitric acid has an acid concentration of between 95 and 100 weight percent.

12. The process of claim 1 wherein said anhydrous nitric acid has an acid concentration of at least 98 weight percent.

13. The product mixture produced by the process of claim 1 which is free of mononitro- and dinitrocresol species.

14. A process for nitrating toluene to produce dinitrotoluene in a product mixture that is free of mononitro- and dinitrocresol by a liquid phase nitration reaction effected in less than 15 minutes by reacting nitric acid with toluene in the absence of sulfuric acid, and in the absence of any aprotic dipolar solvent during the reaction and in the absence of any aprotic dipolar solvent to halt the reaction, in a reactor at a reaction temperature of between 0° C. and 60° C. and a reaction pressure not exceeding atmospheric pressure, said nitric acid having an acid content of between 95 and 100 percent by weight based upon the weight of acid plus water therein, the molare ratio of nitric acid plus water to toluene being between 10:1 and 15:1.

* * * * *